(12) United States Patent
Hartwig et al.

(10) Patent No.: US 7,989,496 B2
(45) Date of Patent: Aug. 2, 2011

(54) TRANSDERMAL DELIVERY OF KETOPROFEN POLAR DERIVATIVES

(75) Inventors: Rod Hartwig, Miami, FL (US); David Houze, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 293 days.

(21) Appl. No.: 11/924,371

(22) Filed: Oct. 25, 2007

(65) Prior Publication Data
US 2009/0062394 A1    Mar. 5, 2009

Related U.S. Application Data

(60) Provisional application No. 60/854,692, filed on Oct. 27, 2006.

(51) Int. Cl.
*A01N 37/10* (2006.01)
*A61K 31/235* (2006.01)

(52) U.S. Cl. .................................. 514/532; 514/817
(58) Field of Classification Search .................. 514/532, 514/817

See application file for complete search history.

(56) References Cited

U.S. PATENT DOCUMENTS

| | | |
|---|---|---|
| 4,390,520 A | 6/1983 | Nagai et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,994,267 A | 2/1991 | Sablotsky |
| 5,474,783 A | 12/1995 | Miranda et al. |
| 5,656,386 A | 8/1997 | Scherer et al. |
| 5,958,446 A | 9/1999 | Miranda et al. |
| 6,562,363 B1 | 5/2003 | Mantelle et al. |
| 2005/0019385 A1 | 1/2005 | Houze |
| 2005/0118247 A1 | 6/2005 | Cordes et al. |
| 2006/0233870 A1 | 10/2006 | Houze et al. |

FOREIGN PATENT DOCUMENTS

| | | |
|---|---|---|
| EP | 0 607 434 A1 | 7/1994 |
| EP | 0 827 741 A2 | 3/1998 |
| WO | WO 2004/082580 | 9/2004 |

OTHER PUBLICATIONS

Hartwig R, Bonne S, and Sintas J, "Transdermal Drug Delivery of Ketoprofen Esters Through Human Cadaver Skin," The AAPS Joournal, Oct. 2005, 7(S2).*
Hartwig R, Bonne S, and Sintas J, "Transdermal Drug Delivery of a Polar Derivative of Ketoprofen Free Acid Through Human Cadaver Skin," The AAPS Joournal, Oct. 2006, 8(S2).*
Rautio J, Taipale H, Gynther J, Vepsalainen J, Nevalainen T, and Jarvinen T, "In vitro evaluation of acyloxyalkyl esters as dermal prodrugs of ketoprofen and naproxen," Journal of Pharmaceutical Sciences, Dec. 1998, 87(12), 1622-1628.*
van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*
International Search Report, dated Mar. 3, 2009, issued for International Application No. PCT/US2007/082494.

* cited by examiner

*Primary Examiner* — San-Ming Hui
*Assistant Examiner* — Paul Zarek
(74) *Attorney, Agent, or Firm* — Foley & Lardner LLP (57) ABSTRACT

A topical or transdermal composition including a polar derivative of ketoprofen and a pharmaceutically acceptable topical or transdermal carrier, wherein the polar derivative of ketoprofen comprises a polarity that is greater than that of ketoprofen.

18 Claims, 2 Drawing Sheets

TRANSDERMAL DELIVERY OF KETOPROFEN POLAR DERIVATIVES

RELATED APPLICATIONS

This application claims the benefit of priority under 35 U.S.C. §119(e) to U.S. provisional application 60/854,692, filed Oct. 27, 2006, the entire contents of which are incorporated by reference herein in its entirety.

FIELD OF THE INVENTION

The present invention is directed to compositions for topical or transdermal delivery of active pharmaceutical agents and methods of using the compositions. In particular, the active pharmaceutical agent may comprise a polar ketoprofen derivative and optionally ketoprofen and/or non-polar ketoprofen derivatives.

BACKGROUND

The use of a dermal drug delivery composition, such as a topical, transdermal, or transmucosal composition containing a medicament (e.g. a drug), as a means for administering locally or systemically therapeutically effective amounts of the medicament is well known. Exemplary topical compositions include liquids, creams, lotions, salves, pastes, balms, gels and ointments. Exemplary transdermal or transmucosal compositions include flexible-finite systems, such as patches. A typical patch may comprise a transdermal carrier, such as a polymeric pressure-sensitive adhesive or bioadhesive composition, and the medicament. In some cases, the medicament is comprised in the transdermal carrier, such as by the formation of a dispersion, solution or blend of the transdermal carrier formulation and the drug. When the transdermal carrier comprises an adhesive, such as a pressure-sensitive adhesive or bioadhesive, the adhesive functions to adhere the composition directly to the skin or mucosa. Generally, the adhesive adheres effectively to the skin or mucosa and permits migration of the medicament from the carrier to the site of application and/or through the skin or mucosa and into the bloodstream of the patient.

Topical or transdermal (or transmucosal) drug delivery permits controlled release of a drug into a patient without directly invading the patient's body. This mode of administration can conveniently and effectively deliver drug doses in a passive and continuous manner over the course of hours, days, or weeks. Typically, a transdermal drug delivery composition can be placed anywhere on the skin, including sites typically concealed by clothing, and is therefore discreet and cosmetically elegant. Its ease of use also increases patient compliance with drug administration. For example, an individual does not have to adhere to a strict oral regimen, perform routine injections or travel to a clinic for treatment.

Topical and transdermal delivery compositions can be designed to achieve particular blood level profiles of the drug, such as steady-state blood level profiles or increasing blood level profiles, such as may be desired for a particular drug or condition. Moreover, the release rate of the drug can be controlled, for example, by the selection of the polymers used in the carrier composition and other components, such as permeation enhancers, crystallization inhibitors, and other components that are well known in the art.

For these and other reasons, a topically or transdermally formulated drug is often perceived as more desirable than traditional drug delivery systems, such as injections and orally-administered tablets. However, it can be difficult to formulate a drug into a composition that will effectively pass through the outer layers of the skin for therapeutically effective administration. For example, non-polar drugs, insoluble drugs, drugs that crystallize in the presence of typical topical or transdermal compositions, and drugs that react with or degrade in the presence of typical topical or transdermal compositions present particular challenges in the context of topical or transdermal administration.

Ketoprofen is a member of the non-steroidal anti-inflammatory drug (NSAIDs) family. The chemical name is 2-(3-benzoyl-phenyl)-propionic acid and the chemical structure is shown below as Formula I:

Formula I

Ketoprofen is a carboxylic acid compound that readily crystallizes. The crystallization and acid character of ketoprofen present challenges in the preparation of topical or transdermal compositions comprising ketoprofen.

Previous work by the inventor explored the transdermal delivery rate of non-polar ketoprofen derivatives, and found that methyl, ethyl, and isopropyl esters of ketoprofen achieved lower delivery rates than ketoprofen.

SUMMARY

One embodiment provides a topical or transdermal composition comprising (a) a polar ketoprofen derivative and (b) a pharmaceutically acceptable topical or transdermal carrier, wherein the polar ketoprofen derivative comprises a polarity that is greater than that of ketoprofen. In specific embodiments, the polar ketoprofen derivative is a polar prodrug of ketoprofen.

In some embodiments, the polar ketoprofen derivative is an ester of ketoprofen, such as represented by formula II:

Formula II wherein R is a polar substituent. In some embodiments, R comprises at least one hydroxyl group, or R may comprise at least two hydroxyl groups. In specific embodiments, the polar ketoprofen derivative is selected from the group consisting of methylene glycol ketoprofen derivatives, ethylene glycol ketoprofen derivatives, propylene glycol ketoprofen derivatives, isopropylene glycol ketoprofen derivatives, butylene glycol ketoprofen derivatives, alpha hydroxy acid ketoprofen derivatives, lactic acid ketoprofen derivatives and glycolic acid ketoprofen derivatives, or is ketoprofen glycerol monoester.

In some embodiments, the polar ketoprofen derivative has a molecular weight that is less than about 1.3 times the molecular weight of ketoprofen.

In some embodiments, the polar ketoprofen derivative has a $K_{OW}$ value that is lower than a $K_{OW}$ value of ketoprofen, when measured under comparable conditions.

In some embodiments, the composition comprises a therapeutically effective amount of polar ketoprofen derivative.

In some embodiments the composition comprises a mixture of polar ketoprofen derivatives. In some embodiments the composition further comprises ketoprofen. In some embodiments, the composition further comprises at least one non-polar ketoprofen derivative.

In some embodiments, the composition achieves a transdermal delivery rate of ketoprofen derivative that is at least about 20% of the delivery rate achieved by a corresponding composition comprising an equivalent amount of ketoprofen, when assessed under comparable conditions.

Another embodiment provides a method of providing ketoprofen therapy comprising administering to a patient in need thereof a topical or transdermal composition comprising (a) a polar ketoprofen derivative and (b) a pharmaceutically acceptable topical or transdermal carrier, wherein the polar ketoprofen derivative comprises a polarity that is greater than that of ketoprofen. In some embodiments, the composition further comprises ketoprofen. In some embodiments, the composition further comprises a non-polar ketoprofen derivative.

DETAILED DESCRIPTION

The present invention provides topical and transdermal compositions comprising a polar derivative of ketoprofen. The compositions are useful, for example, in methods of providing ketoprofen therapy to a patient in need thereof.

A. DEFINITIONS

For the purposes of this disclosure and unless otherwise specified, "a" or "an" means "one or more."

As used herein, "about" will vary to some extent depending upon the context in which it is used. In general, "about" may mean up to plus or minus 10% of the particular term.

As used herein, "acrylic-based" polymer means any acrylic polymer suitable for use in a transdermal compositions, such as polyacrylate, polyacrylic, acrylate and acrylic polymers. Acrylic-based polymers include homopolymers, copolymers, terpolymers, and the like of various acrylic acids or ester, including polymers of one or more monomers of acrylic acids and other copolymerizable monomers, copolymers of alkyl acrylates and/or methacrylates and/or copolymerizable secondary monomers, and acrylic-based polymers with functional groups are copolymerized with functional monomers.

The term "administering" or "administration" is intended to mean any mode of application to a tissue which results in the physical contact of the composition with an anatomical site or surface area.

The term "bioadhesives" as used herein mean natural, synthetic or semi-synthetic materials that adhere and preferably strongly adhere to a surface such as skin, teeth or mucous membrane upon wetting or hydration. Typically, a bioadhesive is capable of maintaining close or intimate contact with a wet or moist surface for an amount of time.

As used herein, the term "flux" is defined as the absorption of the active agent through the skin or mucosa, and is described by Fick's first law of diffusion:

$$J = -D(dC_m/dx),$$

where J is the flux in $g/cm^2/sec$, D is the diffusion coefficient of the drug through the skin or mucosa in $cm^2/sec$ and $dC_m/dx$ is the concentration gradient of the active agent across the skin or mucosa.

As used herein, the term "ketoprofen therapy" means the administration of one or more drugs with ketoprofen activity to achieve the pharmaceutical effects of ketoprofen in vivo, such as by the administration of one or more ketoprofen derivatives (such as ketoprofen prodrugs) or a combination of one or more ketoprofen derivatives and ketoprofen.

As used herein, the term "parent drug" refers to the free acid form of ketoprofen.

As used herein, a "prodrug" refers to a derivative of a parent drug that exhibits a similar therapeutic effect as the parent drug upon administration. In some cases, the prodrug undergoes biotransformation, either spontaneous or enzymatic, upon administration to convert to a therapeutically active form. For example, a prodrug may comprise chemical groups that are cleavable under metabolic conditions. Prodrugs of various drugs are known in the art. For example, prodrugs may be esters prepared by reaction of the parent acids with a suitable alcohol or amides prepared by reaction of the parent acid compound with an amine or basic groups reacted to form an acylated base derivative. See, Bundgard, Design of Prodrugs, pp. 7-9, 21-24, Elsevier, Amsterdam 1985; Silverman, The Organic Chemistry of Drug Design and Drug Action, pp. 352-401, Academic Press, San Diego, Calif., 1992; and Burger's Medicinal Chemistry and Drug Chemistry, Fifth Ed., Vol. 1, pp. 172-178, 949-982 (1995).

The term "patient" refers to animals, including humans, in need of ketoprofen therapy.

As used herein, the phrase "therapeutically effective amount" means an amount (dosage) that achieves the specific pharmacological response for which the drug is administered in a given patient. It is emphasized that a "therapeutically effective amount" of a drug that is administered to a particular subject in a particular instance may not always be effective in treating the target conditions/diseases, even though such dosage is deemed to be a therapeutically effective amount by those of skill in the art. Those skilled in the art will recognize that the "therapeutically effective amount" may vary from patient to patient, or from condition to condition, and can determine a "therapeutically effective amount" for a given patient/condition by routine means.

The term "topical" or "topically" is used herein in its conventional meaning as referring to direct contact with a site on a patient, which can be any anatomical site or surface including skin or mucous membranes.

B. KETOPROFEN AND KETOPROFEN DERIVATIVES

Compositions described herein comprise a polar derivative of ketoprofen and a pharmaceutically acceptable topical or transdermal carrier, wherein the polar derivative of ketoprofen comprises a polarity that is greater than that of ketoprofen. In some embodiments, the polar derivative of ketoprofen is a polar prodrug of ketoprofen.

Suitable polar derivatives of ketoprofen include, but are not limited to, esters of ketoprofen. For example, ketoprofen esters include those represented by formula II:

Formula II wherein R is a polar substituent. Such polar substituents may include at least one hydroxyl group, at least two hydroxyl groups, or more than two hydroxyl groups. Exemplary R groups may also include $C_{1-6}$ alkyl groups substituted with at least one hydroxyl group, at least two hydroxyl groups, or more than two hydroxyl groups. Exemplary derivatives include methylene glycol derivatives, ethylene glycol derivatives, propylene glycol derivatives (including isopropyl glycol derivatives), and butylene glycol derivatives. Other exemplary derivatives include alpha hydroxy acid derivatives, such as lactic acid and glycolic acid derivatives. In some embodiments, the polar derivative of ketoprofen is ketoprofen glycerol monoester.

Esters of ketoprofen, such as those identified by Formula II, may be prepared via an esterification reaction between the free acid (ketoprofen) and an alcohol in the presence of an acid catalyst. While not wanting to be bound by any theory, it is believed that the esterification reaction may be reversed under metabolic conditions to free the ketoprofen active ingredient and a pharmaceutically safe excipient. For example, the de-esterification of the mono-glycerol ester of ketoprofen in the body converts the ester into ketoprofen and glycerin.

It is generally believed that drugs with higher molecular weights achieve lower delivery rates. Thus, for example, the lower delivery rates of the methyl, ethyl, and propyl ester derivatives of ketoprofen previously prepared may be due, at least in part, to their higher molecular weights.

While not wanting to be bound by any theory, it is believed that, in accordance with the present invention, providing a polar ketoprofen derivative may at least partially, and in some cases fully, compensate for the effects of molecular weight. Thus, for example, it is believed that a polar ketoprofen derivative will achieve a faster delivery rate than a non-polar derivative of the same molecular weight. Thus, it is believed that polar ketoprofen derivatives will achieve satisfactory delivery rates, even if the rates are lower than that achieved by the free acid form of ketoprofen.

As shown below, a polar derivative of ketoprofen, the mono-glycerol ester, achieves a faster delivery rate than each of the non-polar ester derivatives tested, even though it has a higher molecular weight. The mono-glycerol ester has a molecular weight that is approximately 29% greater than ketoprofen, or that is about 1.3 times that of ketoprofen. In some embodiments, the polar derivative of ketoprofen has a molecular weight that is less than about 1.3 times the molecular weight of ketoprofen.

In some embodiments, the composition comprises both one or more polar derivatives of ketoprofen and the free acid form of ketoprofen (i.e., "ketoprofen"). The relative amounts of derivative: parent drug can be selected to balance the stability and delivery properties of the composition. For example, while not wanting to be bound by any theory, it is believed that a composition that comprises more ketoprofen may exhibit less stability, while a composition that comprises more polar ketoprofen derivative may exhibit a lower delivery rate.

In some embodiments, the composition comprises both one or more polar derivatives of ketoprofen and one or more non-polar derivatives of ketoprofen. In some embodiments, the non-polar derivatives of ketoprofen are a non-polar prodrugs of ketoprofen. Exemplary non-polar ketoprofen derivatives include methyl, ethyl, propyl, isopropyl and butyl esters of ketoprofen. The relative amounts of polar and non-polar derivatives can be selected to balance the properties of the composition, such as stability and delivery properties. Compositions comprising both polar and non-polar ketoprofen derivatives also may further comprise the free acid form of ketoprofen (i.e., "ketoprofen").

The composition may comprise from 0.1-100% polar ketoprofen derivative, based on the total weight of polar ketoprofen derivative, non-polar ketoprofen derivative, and ketoprofen present. Exemplary combination compositions may comprise at least 10% polar ketoprofen derivative, at least 20% polar ketoprofen derivative, at least 25% polar ketoprofen derivative, at least 30% polar ketoprofen derivative, at least 40% polar ketoprofen derivative, at least 50% polar ketoprofen derivative, at least 60% polar ketoprofen derivative, at least 70% polar ketoprofen derivative, at least 75% polar ketoprofen derivative, at least 80% polar ketoprofen derivative, at least 90% polar ketoprofen derivative, at least 95% polar ketoprofen derivative, or at least 99% polar ketoprofen derivative.

The composition may comprise from 0.1-100% combined ketoprofen derivatives (e.g., polar and non-polar), based on the total weight of polar ketoprofen derivative, non-polar ketoprofen derivative, and ketoprofen present. Exemplary combination compositions may comprise at least 10% ketoprofen derivatives, at least 20% ketoprofen derivatives, at least 25% ketoprofen derivatives, at least 30% ketoprofen derivatives, at least 40% ketoprofen derivatives, at least 50% ketoprofen derivatives, at least 60% ketoprofen derivatives, at least 70% ketoprofen derivatives, at least 75% ketoprofen derivatives, at least 80% ketoprofen derivatives, at least 90% ketoprofen derivatives, at least 95% ketoprofen derivatives, or at least 99% ketoprofen derivative. The derivative component may comprise from 0.1-100% polar ketoprofen derivative, based on the total weight of polar ketoprofen derivative and non-polar ketoprofen derivative present, such as at least 10%, at least 20%, at least 25%, at least 30%, at least 40%, at least 50%, at least 60%, at least 70%, at least 75%, at least 80%, at least 90%, at least 95%, or at least 99% polar ketoprofen derivative, out of the total amount of ketoprofen derivatives present.

The compositions may comprise a therapeutically effective amount of the polar ketoprofen derivative and, in combination embodiments, may also comprise a therapeutically effective amount of the non-polar ketoprofen derivative and/or a therapeutically effective amount of ketoprofen. The therapeutically effective amount of ketoprofen derivative(s) and/or ketoprofen may vary depending on the specific patient, the desired therapeutic effect, and the duration of the therapy. A composition may comprise from about 0.1% to about 90%, including from about 0.1% to about 50%, by weight of ketoprofen derivative(s) and/or ketoprofen, based on the weight of the composition.

As noted above, the composition may comprise one or more polar ketoprofen derivatives, one or more non-polar ketoprofen derivatives, and/or ketoprofen. In such combination compositions, any one or more of the ketoprofen derivative(s) and/or ketoprofen may be present in an amount that would be therapeutically effective in a corresponding composition comprising only the ketoprofen derivative or ketoprofen as the active ingredient. In other embodiments, at least one of the ketoprofen derivative(s) or ketoprofen is present in an amount that would not be therapeutically effective in a corresponding composition comprising only the ketoprofen derivative or ketoprofen as the active ingredient. In other embodiments, each of the ketoprofen derivative(s) and ketoprofen are present in an amount that would not be therapeutically effective in a corresponding composition comprising only the ketoprofen derivative or ketoprofen as the active ingredient. In such embodiments, the composition may nevertheless provide a therapeutic effect (e.g., provide ketoprofen therapy) because of the combined effect of the ketoprofen derivative(s) and ketoprofen.

C. POLARITY OF KETOPROFEN AND KETOPROFEN DERIVATIVES

The octanol-water partition coefficient ($K_{OW}$) is a measure of the equilibrium concentration of a compound between octanol and water, and the log $K_{OW}$ is used to express the coefficient as a small integer. When comparing the polarity of compounds based upon the value of their respective log $K_{OW}$ values, those compounds with greater polarity will have a lower log $K_{OW}$ value than those of lesser polarity. As shown experimentally below, ketoprofen derivatives having a greater polarity (i.e. a lower log $K_{OW}$ value) may exhibit greater skin permeation (e.g., greater delivery rates) than ketoprofen derivatives that are less polar.

In one embodiment the polar ketoprofen derivative exhibits a lower log $K_{OW}$ value than ketoprofen, when measured under comparable conditions, such as by the procedures outlined in the examples below. For example, the polar ketoprofen derivative may exhibit a log $K_{OW}$ value that is about ⅔ or 67% that of ketoprofen. In other embodiments, the polar ketoprofen derivative exhibits a log $K_{OW}$ value that is less than about 95%, less than about 90%, less than about 80%, less than about 75%, less than about 70%, less than about 60%, less than about 50%, less than about 40%, less than about 30%, less than about 20%, or less than about 10% that of ketoprofen.

Figure 1:
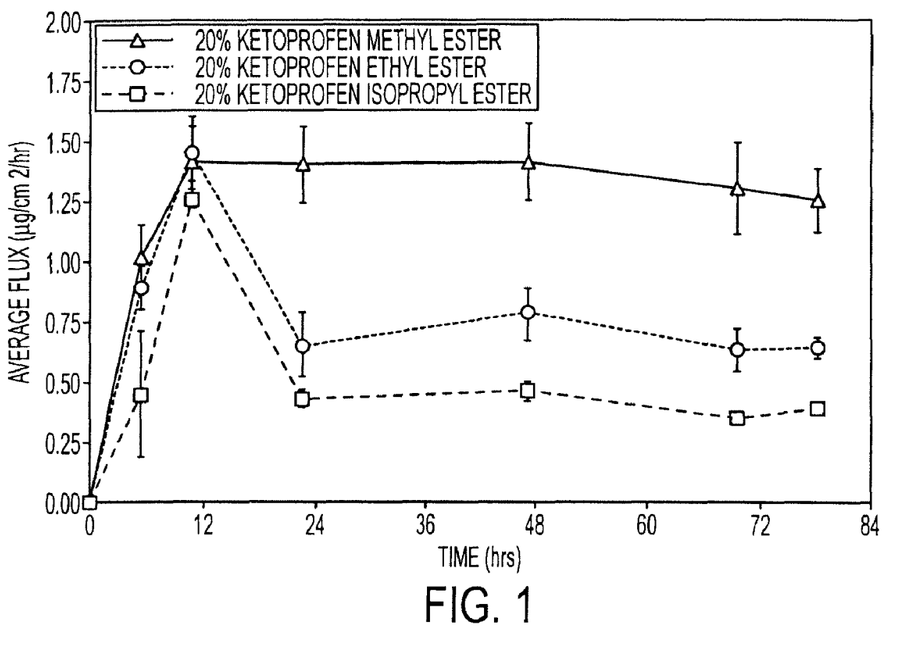
FIG. 1 is a graph showing the average flux of non-polar derivatives of ketoprofen through cadaver skin.
Figure 2:
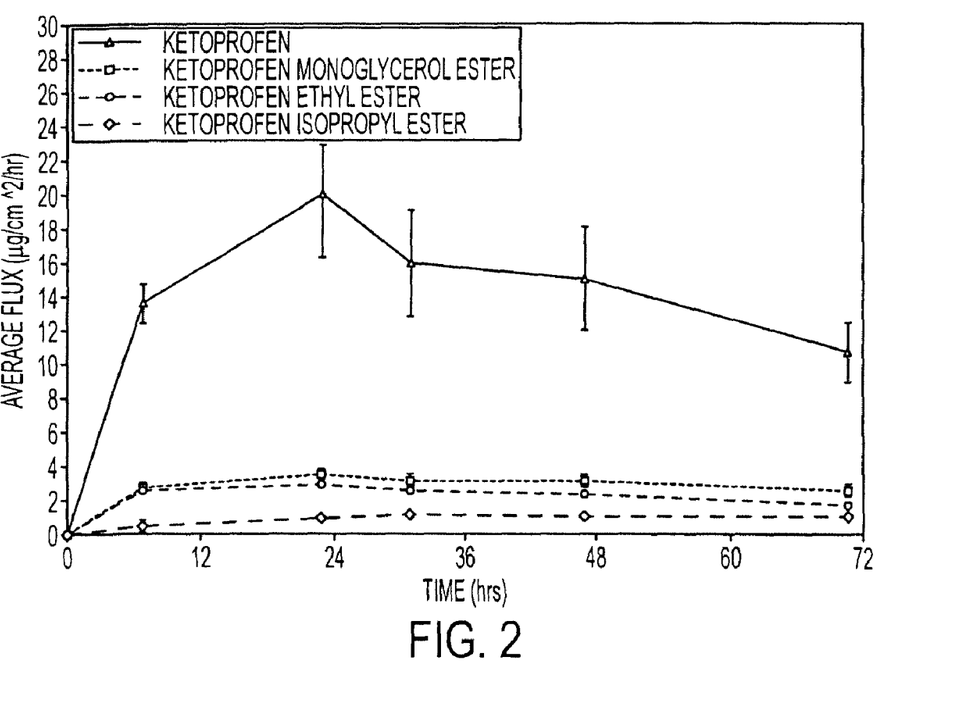
FIG. 2 is a graph showing the average flux of ketoprofen and both polar and non-polar derivatives of ketoprofen through cadaver skin.

Transdermal delivery through human skin is assessed in vitro using, for example, human cadaver skin in Franz cells. FIGS. 1 and 2, below as well as Table 1, illustrate the time-dependent flux of ketoprofen and several ketoprofen derivatives (esters) through cadaver skin in Franz cells. These measurements provide an indication of the ability of the drug to permeate the skin and be effectively delivered transdermally.

FIG. 1 illustrates the average flux of non-polar ketoprofen derivatives over an approximate 84 hour time period. The drug delivery profiles are consistent with the hypothesis that the higher the molecular weight of the derivative, the lower the delivery rate. For example, FIG. 1 illustrates that the methyl ester of ketoprofen has a faster delivery rate than each of the ethyl ester and isopropyl ester.

FIG. 2 illustrates the average flux of a polar ketoprofen derivative, non-polar ketoprofen derivatives, and ketoprofen. The ketoprofen achieves the highest delivery rate, and the polar derivative achieves a higher delivery rate than either of the two non-polar derivatives tested, even though the polar derivative has a higher molecular weight.

In some embodiments, the composition comprising a polar ketoprofen derivative achieves a transdermal delivery rate that is at least about 20% of the delivery rate of ketoprofen, as measured under comparable conditions, such as by the procedures using human cadaver skin in Franz cells outlined in the examples below. In other embodiments, the delivery rate of the ketoprofen derivative is at least about 25% of the delivery rate of ketoprofen, at least about 30% of the delivery rate of ketoprofen, at least about 40% of the delivery rate of ketoprofen, at least about 50% of the delivery rate of ketoprofen, at least about 60% of the delivery rate of ketoprofen, at least about 70% of the delivery rate of ketoprofen, at least about 75% of the delivery rate of ketoprofen, at least about 80% of the delivery rate of ketoprofen, at least about 90% of the delivery rate of ketoprofen, at least about 95% of the delivery rate of ketoprofen, or at least about 99% of the delivery rate of ketoprofen. In other embodiments, the delivery rate of the ketoprofen derivative is equal to or greater than the delivery rate of ketoprofen, as measured under comparable conditions.

In some embodiments, the composition achieves a skin permeation of the polar derivative of ketoprofen that is greater than about 100 µg/cm² over a period of 72 hours. For example, the skin permeation may be at least about 100 µg/cm² over 72 hours; at least about 150 µg/cm² over 72 hours; at least about 200 µg/cm² over 72 hours; at least about 250 µg/cm² over 72 hours; at least about 300 µg/cm² over 72 hours; at least about 350 µg/cm² over 72 hours; at least about 400 µg/cm² over 72 hours; at least about 450 µg/cm² over 72 hours; at least about 500 µg/cm² over 72 hours; at least about 550 µg/cm² over 72 hours; at least about 600 µg/cm² over 72 hours; at least about 650 µg/cm² over 72 hours; at least about 700 µg/cm² over 72 hours; at least about 750 µg/cm² over 72 hours; at least about 800 µg/cm² over 72 hours; at least about 850 µg/cm² over 72 hours; at least about 900 µg/cm² over 72 hours; at least about 950 µg/cm² over 72 hours; at least about 1000 µg/cm² over 72 hours; at least about 1100 µg/cm² over 72 hours, where the skin permeation of ketoprofen is about 1110 µg/cm² over 72 hours. In other embodiments, the composition achieves a skin permeation of the ketoprofen derivative that is equal to or greater than that achieved by a comparable composition comprising ketoprofen, as measured under comparable conditions.

D. TOPICAL & TRANSDERMAL CARRIERS

The present invention is not limited to any specific type of topical or transdermal carrier, but is useful in connection with any pharmaceutically acceptable topical or transdermal carrier. Thus, the following is provided as general guidelines only, and is not intended to limit the scope of the invention in any way.

Topical Carriers

In some embodiments, the composition comprises a topical carrier. Exemplary topical carriers include liquids, creams, lotions, salves, balms, pastes, gels and ointments.

Ointments are typically semisolid preparations that are often based on petrolatum or other petroleum derivatives. As with other carriers or vehicles, an ointment base may be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases.

Creams also are well known in the art, and include viscous liquids or semisolid emulsions, either oil-in-water or water-in-oil. Cream bases typically are water-washable, and usually contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Gels are typically semisolid, suspension-type systems. Single-phase gels may contain organic macromolecules distributed substantially uniformly throughout the carrier liquid, which is typically aqueous, but also may contain an alcohol and/or an oil. Exemplary gelling agents include crosslinked acrylic acid polymers such as the "carbomer" family of polymers, e.g., carboxypolyalkylenes that may be obtained commercially under the Carbopol® trademark. Also known are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are typically preparations to be applied to the skin surface without friction, and are often liquid or semiliquid preparations in which solid particles, including the active agent, are present in a water or alcohol base. Lotions are usually suspensions of solids, and may comprise a liquid oily emulsion of the oil-in-water type. The insoluble matter in a lotion may be finely divided. Lotions may contain suspending agents to produce better dispersions, as well as compounds useful for localizing and holding the active agent in contact with the skin, e.g., methylcellulose, sodium carboxymethylcellulose, or the like.

Pastes are typically semisolid dosage forms in which the active agent is suspended in a suitable base. Depending on the nature of the base, pastes may be fatty pastes or may be made from single-phase aqueous gels. The base in a fatty paste is generally petrolatum or hydrophilic petrolatum or the like. The pastes made from single-phase aqueous gels generally incorporate carboxymethylcellulose or the like as a base.

Transdermal Carriers

In some embodiments, the composition comprises a transdermal carrier. Exemplary transdermal carriers include flexible, finite systems, such as transdermal patches.

The phrase "flexible, finite system" is intended to mean a solid form capable of conforming to the surface with which it comes into contact, and which is capable of maintaining the contact in such solid form so as to facilitate topical or transdermal application without adverse physiological response, and without being appreciably decomposed by aqueous contact during administration to a patient. Particular flexible, finite systems include polymer carriers such as the pressure-sensitive adhesive matrix type in which the drug is dispersed directly in the pressure-sensitive adhesive, or reservoir type carriers. Illustrative examples of suitable adhesives as matrix type flexible, finite delivery systems include those described in U.S. Pat. Nos. 5,474,783, and 5,656,386. Other flexible, finite systems include films, plasters, dressings, and bandages, as well as multilayer delivery systems in which the drug is solubilized or contained in one or more separate layers, and reservoir-type delivery systems in which the drug is solubilized or contained in a reservoir or depot separate from the adhesive which attaches directly to the skin or mucosa.

Thus, in some embodiments, the pharmaceutically acceptable transdermal carrier comprises an adhesive. Suitable adhesives are known in the art and include pressure-sensitive adhesives and bioadhesives.

Bioadhesive materials useful in some embodiments include those described in U.S. Pat. No. 6,562,363. For example, bioadhesive materials may include polymers, either water soluble or water insoluble, with or without crosslinking agents, which are bioadhesive. Exemplary bioadhesives include natural materials, cellulose materials, synthetic and semi-synthetic polymers, and generally, any physiologically acceptable polymer showing bioadhesive properties, or mixtures of any two or more thereof.

Pressure sensitive adhesives suitable for use in accordance with the invention include, but are not limited to, pressure-sensitive silicone adhesives, pressure-sensitive acrylic adhesives, and mixtures of any two or more thereof.

Exemplary pressure-sensitive silicone adhesives include polysiloxanes and other silicone adhesives as disclosed in U.S. Pat. Nos. 4,591,622; 4,584,355; 4,585,836; 4,655,767; 5,958,446; in co-pending U.S. patent application Ser. No. 10/895,688; and in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989). Suitable silicone pressure-sensitive adhesives are commercially available and include the silicone adhesives sold under the trademarks BIO-PSA X7-3027, BIO-PSA X7-4919, BIO-PSA X7-2685, and BIO-PSA X7-3122 by Dow Corning Corporation, Medical Products, Midland, Mich.

Suitable acrylic-based pressure-sensitive adhesives are also known in the art. Such acrylic-based polymers may be used as the primary pressure-sensitive adhesive (see, e.g., U.S. Pat. No. 4,390,520), or may be used in combination with other polymers which may or may not be pressure-sensitive adhesives (see, e.g. U.S. Pat. No. 4,994,267). Acrylic-based pressure-sensitive adhesives may be polymerized with functional monomers to provide functional groups on the acrylic-based adhesive, such as may be desired to improve wear properties and drug delivery. Suitable polyacrylic acid polymers include polymers of acrylic acid crosslinked with polyalkenenyl ethers (generically known as carbomers) or divinyl glycol (generically known as polycarbophils) and commercially available from B. F. Goodrich, Cincinnati, Ohio, under the trademark Carbopol® copolymers or resins such as Carbopol® 934 NF, 934P NF, 940 NF and 971P NF, Pemulen polymeric emulsifiers and Noveon polycarbophils. Other pressure-sensitive adhesive acrylic polymers are described in U.S. Patent Application Number 2006/0233870.

Polymer blends as described in U.S. Pat. No. 5,958,446 may also be used as pharmaceutically acceptable carriers and adhesives in the transdermal compositions embodied herein.

In certain embodiments of the invention a plasticizer or tackifying agent is incorporated into the formulation to improve the adhesive characteristics of the composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is preferably compatible with the blend of polymers. In some embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where polyacrylate, for example, is a major component, mineral oil may be used as a tackifying agent.

Those skilled in the art will appreciate that suitable compositions may also contain agents known to accelerate the delivery of the drug through the skin. Such agents have been referred to as skin-penetration enhancers, accelerants, adjuvants, and sorption promoters, and are collectively referred herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug. Some exemplary agents are listed in U.S. Pat. Nos. 5,958,446 and 6,562,363.

Those skilled in the art will appreciate that the composition can contain other components, including other functional and inert components, that are known in the art for use in topical or transdermal compositions.

The topical or transdermal compositions can be made in accordance with methods known in the art, such as by blending the ketoprofen derivative (and, optionally, ketoprofen) with the pharmaceutically acceptable topical or transdermal carrier components, or by dissolving the ketoprofen derivative (and, optionally, ketoprofen) in a solvent and combining the solution with the pharmaceutically acceptable topical or transdermal carrier components, or by other conventional methods.

In some embodiments, a transdermal composition is applied to a substrate, to form a flexible, finite system, such as a transdermal patch. In some embodiments, the substrate is laminated to one or more additional layers, such as a protective layer, a backing layer, a rate-controlling layer, a membrane layer, or one or more other types of layers known in the art.

Those skilled in the art will readily realize that all ranges and ratios discussed herein can and do necessarily also describe all subranges and subratios therein for all purposes and that all such subranges and subratios also form part and parcel of this invention. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

Examples

Esters of ketoprofen were prepared via reaction with a corresponding alcohol in the presence of an acid catalyst. For example, ketoprofen was reacted with one of the following alcohols: glycerol (99.5%), anhydrous ethyl alcohol (200 proof), or isopropyl alcohol. The esterification was carried out by refluxing ketoprofen and the alcohol under heat and an acid catalyst to drive the equilibrium reaction toward the product ester. Purification of the products was achieved using low pressure normal phase liquid chromatography. Thin layer chromatography (TLC) and high performance liquid chromatography (HPLC) techniques were utilized to establish purity and potency of the esters. Since standards of the ester materials were not available a response factor of 1:1 was assumed and the potencies were based on the ketoprofen reference standard.

TABLE I

Ketoprofen Ester Modification:

| Active Drug | Molecular Weight | Calculated Log $K_{OW}$* | 72 hr Cumulative Permeation (mg/cm$^2$) |
|---|---|---|---|
| Ketoprofen | 254.29 | 3.00 | 1110.0 |
| Ketoprofen Monoglycerol Ester | 328.37 | 2.04 | 214.4 |
| Ketoprofen Ethyl Ester | 282.34 | 4.14 | 169.7 |
| Ketoprofen Isopropyl Ester | 296.37 | 4.56 | 61.2 |

*Calculated by EPI Suite Software, KOWWIN v1.67, © 2000.

Blend to Laminate Production:

Laboratory purified ketoprofen esters were isolated and incorporated into drug-in-adhesive formulations for evaluation. Formulations were prepared with the above-prepared ketoprofen esters in equivalent concentrations of silicone pressure-sensitive adhesive and acrylic pressure-sensitive adhesive, to assess penetration through human cadaver skin. After the formulations were prepared, it was determined that lower than ideal purity of the ketoprofen esters caused the formulations to have differing concentrations of the ketoprofen derivative, which prevents a precise evaluation and a 1:1 comparison of drug delivery rates.

All blends were prepared in an ethyl acetate solvent system to create homogeneous polymer blends. The homogeneous blends were cast with a wet-gap, draw-down applicator bar onto a fluoropolymer-coated polyester release liner. The draw-down casts were dried for 5 minutes at ambient room temperature under a hood, and for 5 minutes at 92° C. in a convection air oven. Upon completion of drying, the dry adhesive was laminated to the ethylene/vinyl acetate side of a polyester/ethylene vinyl acetate backing. The end product had a dry coat weight of approximately 10 mg/cm$^2$.

Human Cadaver Skin Permeation Study:

A human cadaver skin permeation study was performed to determine the skin penetration of ketoprofen and ketoprofen esters through the stratum corneum barrier layer. The stratum corneum was obtained from split thickness, cryo-preserved cadaver skin by the heat separation technique. Samples of the ketoprofen and ketoprofen ester formulations (5/16 inch diameter) were cut from the above-prepared laminates, in triplicate, and mounted onto pieces of the stratum corneum (½ inch diameter). The samples on the stratum corneum were then placed on modified Franz diffusion cells, in accordance with standard techniques. The receptor phase was 7.5 mL of 0.9% NaCl and 0.01% NaN$_3$ in deionized water. The cells were maintained at 32° C. and were magnetically stirred at approximately 300 rpm. Samples of the receptor phase were taken with complete replacement of the receptor phase at specified time points. The samples were quantified by HPLC. Since standards of the ketoprofen esters were not available, the concentrations of the ketoprofen esters were determined by derivation of the ketoprofen USP standard. The results are presented in Table 1 above and in FIGS. 1 and 2.

While some embodiments have been illustrated and described, it should be understood that changes and modifications can be made therein in accordance with ordinary skill in the art without departing from the invention in its broader aspects as defined in the following claims.

What is claimed is:

1. A topical or transdermal composition comprising:
   (a) a polar ketoprofen derivative; and
   (b) a pharmaceutically acceptable topical or transdermal carrier comprising an adhesive selected from the group consisting of pressure-sensitive adhesives and bioadhesives;
   wherein the polar ketoprofen derivative comprises a polarity that is greater than that of ketoprofen and is represented by formula II:

Formula II wherein R is a $C_{1-6}$ alkyl group substituted with at least two hydroxyl groups.

2. The composition of claim 1, wherein the polar ketoprofen derivative is selected from the group consisting of methylene glycol ketoprofen, ethylene glycol ketoprofen, propylene glycol ketoprofen, isopropylene glycol ketoprofen, butylene glycol ketoprofen, and ketoprofen monoglycerol ester.

3. The composition of claim 1, wherein the polar ketoprofen derivative is ketoprofen glycerol monoester.

4. The composition of claim 1, wherein the polar ketoprofen derivative has a molecular weight that is less than about 1.3 times the molecular weight of ketoprofen.

5. The composition of claim 1, wherein the polar ketoprofen derivative has a $K_{OW}$ value that is lower than a $K_{OW}$ value of ketoprofen, when measured under comparable conditions.

6. The composition of claim 1, wherein the composition comprises a therapeutically effective amount of the polar ketoprofen derivative.

7. The composition of claim 1, further comprising ketoprofen.

8. The composition of claim 7, comprising an amount of the polar ketoprofen derivative that would be therapeutically effective in a corresponding composition comprising only polar ketoprofen derivative as the active ingredient, and an amount of ketoprofen that would be therapeutically effective in a corresponding composition comprising only ketoprofen as the active ingredient.

9. The composition of claim 7, wherein at least one of the polar ketoprofen derivative and ketoprofen is present in an amount that would not be therapeutically effective in a corresponding composition comprising only the ketoprofen derivative or ketoprofen as the active ingredient.

10. The composition of claim 7, wherein both the ketoprofen derivative and ketoprofen are present in amounts that would not be therapeutically effective in a corresponding composition comprising only ketoprofen derivative or ketoprofen as the active ingredient.

11. The composition of claim 1, comprising a mixture of the polar ketoprofen derivatives of claim 1.

12. The composition of claim 1, further comprising at least one non-polar ketoprofen alkyl ester.

13. The composition of claim 1, wherein pharmaceutically acceptable carrier comprises an adhesive selected from the group consisting of pressure-sensitive silicone adhesives and pressure-sensitive acrylic adhesives, and mixtures of any two or more thereof.

14. The composition of claim 1, wherein the pharmaceutically acceptable carrier is provided in a transdermal patch.

15. The composition of claim 1, wherein the composition achieves a transdermal delivery rate of the ketoprofen derivative that is at least about 20% of the delivery rate achieved by a corresponding composition comprising an equivalent amount of ketoprofen, when assessed under comparable conditions.

16. A method of providing ketoprofen therapy comprising administering to a patient in need thereof a topical or transdermal composition comprising:
   (a) a polar ketoprofen derivative; and
   (b) a pharmaceutically acceptable topical or transdermal carrier comprising an adhesive selected from the group consisting of pressure-sensitive adhesives and bioadhesives;
   wherein the polar ketoprofen derivative comprises a polarity that is greater than that of ketoprofen and is represented by formula II:

Formula II wherein R is a $C_{1-6}$ alkyl group substituted with at least two hydroxyl groups.

17. The method of claim 16, wherein the composition further comprises ketoprofen.

18. The method of claim 16, wherein the composition further comprises a non-polar ketoprofen alkyl ester.

* * * * *

UNITED STATES PATENT AND TRADEMARK OFFICE
CERTIFICATE OF CORRECTION

| | | |
|---|---|---|
| PATENT NO. | : 7,989,496 B2 | Page 1 of 1 |
| APPLICATION NO. | : 11/924371 | |
| DATED | : August 2, 2011 | |
| INVENTOR(S) | : Hartwig et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this
Eleventh Day of December, 2012

David J. Kappos
*Director of the United States Patent and Trademark Office*